(12) United States Patent
Capuzzi et al.

(10) Patent No.: US 12,083,202 B2
(45) Date of Patent: *Sep. 10, 2024

(54) LIPOPHILIC COSMETIC COMPOSITIONS CONTAINING PELARGONIC ACID ESTERS

(71) Applicant: Novamont S.p.A., Novara (IT)

(72) Inventors: Luigi Capuzzi, Novara (IT); Francesca Digioia, Novara (IT); Vanessa Bramati, Novara (IT); Federica Carlomagno, Novara (IT); Alessandra Cominetti, Novara (IT)

(73) Assignee: NOVAMONT S.P.A., Novara (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/590,051

(22) Filed: Feb. 1, 2022

(65) Prior Publication Data

US 2022/0151894 A1    May 19, 2022

Related U.S. Application Data

(63) Continuation of application No. 15/758,066, filed as application No. PCT/EP2016/071088 on Sep. 7, 2016, now Pat. No. 11,266,585.

(30) Foreign Application Priority Data

Sep. 8, 2015   (IT) .................. 102015000049554

(51) Int. Cl.
| | | |
|---|---|---|
| *A61K 8/37* | (2006.01) | |
| *A61K 8/06* | (2006.01) | |
| *A61Q 1/00* | (2006.01) | |
| *A61Q 1/02* | (2006.01) | |
| *A61Q 1/06* | (2006.01) | |
| *A61Q 5/06* | (2006.01) | |
| *A61Q 17/04* | (2006.01) | |
| *A61Q 19/00* | (2006.01) | |

(52) U.S. Cl.
CPC ............... *A61K 8/375* (2013.01); *A61Q 1/00* (2013.01); *A61Q 1/02* (2013.01); *A61Q 1/06* (2013.01); *A61Q 5/06* (2013.01); *A61Q 17/04* (2013.01); *A61Q 19/00* (2013.01); *A61K 2800/31* (2013.01)

(58) Field of Classification Search
CPC ...... A61K 8/375; A61K 8/06; A61K 2800/31; A61Q 1/00; A61Q 1/02; A61Q 1/06; A61Q 17/04; A61Q 19/00
See application file for complete search history.

(56) References Cited

U.S. PATENT DOCUMENTS

| | | | |
|---|---|---|---|
| 7,875,263 B1 | 1/2011 | O'Lenick | |
| 10,758,466 B2 * | 9/2020 | Capuzzi ................. | A61K 8/022 |
| 11,039,994 B2 * | 6/2021 | Capuzzi ................. | A61K 8/92 |
| 11,123,274 B2 * | 9/2021 | Capuzzi ................. | A61Q 1/06 |
| 11,266,585 B2 * | 3/2022 | Capuzzi ................. | A61Q 5/06 |
| 11,400,036 B2 * | 8/2022 | Capuzzi ................. | A61Q 19/08 |
| 2004/0126350 A1 | 7/2004 | Blin et al. | |
| 2008/0157022 A1 | 7/2008 | Singh et al. | |
| 2014/0357607 A1 | 12/2014 | Lathrop et al. | |
| 2015/0209429 A9 | 7/2015 | Lathrop et al. | |
| 2018/0177698 A1 | 6/2018 | Capuzzi et al. | |
| 2018/0207071 A1 | 7/2018 | Capuzzi et al. | |
| 2018/0256463 A1 | 9/2018 | Capuzzi et al. | |
| 2019/0192401 A1 | 6/2019 | Capuzzi et al. | |
| 2022/0339085 A1 * | 10/2022 | Capuzzi ................. | A61Q 1/10 |

FOREIGN PATENT DOCUMENTS

| | | |
|---|---|---|
| JP | S52131513 A | 11/1977 |
| JP | S59190907 A | 10/1984 |

OTHER PUBLICATIONS

"Sunscreen SPF 50+", GNPD, Mintel; Oct. 31, 2012; XP-002753094.
"Bb. Shine On (and On . . . ) Finishing Spray", GNPD, Mintel; Jun. 30, 2011; XP-002753100.
First office action issued Oct. 23, 2019 in EP Appln. 16770217.4.

* cited by examiner

*Primary Examiner* — Mina Haghighatian
(74) *Attorney, Agent, or Firm* — POLSINELLI PC

(57) ABSTRACT

Cosmetic lipophilic composition comprising less than 20% by weight of an aqueous component and an oily component characterized in that the oily component comprises at least one ester selected from neopentylglycol dipelargonate, glycerol tripelargonate, pentaerythritol tetrapelargonate or mixtures thereof.

10 Claims, No Drawings

LIPOPHILIC COSMETIC COMPOSITIONS CONTAINING PELARGONIC ACID ESTERS

CROSS REFERENCE TO RELATED APPLICATIONS

This application is a Continuation of Co-pending application Ser. No. 15/758,066, which in turn is a National Phase filing under 35 U.S.C. § 371 of PCT/EP2016/071088 filed on Sep. 7, 2016; application in turn claims priority to Application No. 102015000049554 filed in Italy on Sep. 8, 2015 under 35 U.S.C. § 119. The entire contents of each application are hereby incorporated by reference.

This invention relates to lipophilic cosmetic compositions containing one or more esters selected from neopentyl glycol dipelargonate, glycerol tripelargonate and pentaerythritol tetrapelargonate.

In the cosmetics sector increasing attention has been paid to the identification of new ingredients having a low environmental impact, of natural and renewable origin, and at the same time having excellent functional and sensory properties.

Lipophilic cosmetic compositions, in particular, find application in the care of the skin and hair, and in make-up. These compositions have an oily component, having an emollient and balancing effect, which also has the function of imparting a film-forming effect on products such as, for example, lipsticks, butters and lip glosses, assists the dissolution and dispersion of both chemical and physical filters in sun products and in general helps to disperse colouring agents and other active ingredients.

It has now been observed that esters of pelargonic acid which can be obtained from renewable sources with polyols such as neopentyl glycol, glycerol and pentaerythritol have particular flow and flow and brightening, film-forming and non-unctuous characteristics which render them particularly suitable for use as ingredients of the oily component in lipophilic compositions for cosmetic use, i.e. for the preparation of products intended for application to the outer surface of the human body (epidermis, lips and cutaneous annexes) in order exclusively or mainly to clean them, perfume them, modify their appearance, protect them, maintain them in a good condition or correct body odours. They also have excellent capacity for the dispersion of sun filters, pigments and other additives, whose effects they are capable of potentiating.

The combination of these functional and sensory properties which occur when the abovementioned esters are used both individually and as mixtures also surprisingly makes it possible to use the said esters as the single ingredient of the oily component.

Other advantages deriving from the use of neopentyl glycol dipelargonate, glycerol tripelargonate and pentaerythritol tetrapelargonate as ingredients in lipophilic cosmetic compositions, in addition to those described above, will be obvious to those skilled in the art from reading this application.

The object of this invention is therefore a lipophilic cosmetic composition comprising less than 20% by weight, preferably less than 10%, and more preferably less than 5%, of an aqueous component and an oily component characterised in that the said oily component comprises at least one ester selected from neopentyl glycol dipelargonate, glycerol tripelargonate and pentaerythritol tetrapelargonate or mixtures thereof. According to an aspect of the present invention, compositions comprising at least two esters selected from neopentyl glycol dipelargonate, glycerol tripelargonate, pentaerythritol tetrapelargonate are preferred.

The cosmetic compositions according to the invention preferably comprise 50 to 99% by weight of the said oily component.

Lipophilic cosmetic compositions according to the invention whose oily component comprises at least one of neopentyl glycol dipelargonate and glycerol tripelargonate are preferred; among these, those comprising glycerol tripelargonate are more preferred.

According to one advantageous aspect of the invention the said ester selected from neopentyl glycol dipelargonate, glycerol tripelargonate and pentaerythritol tetrapelargonate is prepared from pelargonic acid from a renewable sources, obtained for example through processes for the oxidative cleavage of vegetable oils, fatty acids and their derivatives, whether modified or not. Preferred examples of renewable sources of pelargonic acid are vegetable oils from sunflowers, brassicaceae or thistles (such as *Cynara cardunculus* and *Silybum marianum*). Particularly preferred sources of pelargonic acid are vegetable oils having a high oleic or erucic acid content. The said pelargonic acid is preferably obtained through oxidative cleavage processes in which inorganic and organic peroxides or peracids, nitric acid, permanganates, periodates, $O_2$, $O_3$ or their gaseous mixtures are used as oxidising agents.

Oxidative cleavage processes in which peroxides such as hydrogen peroxide, and $O_2$ or mixtures containing $O_2$ as oxidising agents are used are preferred. Specific examples are the oxidative cleavage processes described in applications WO 94/10122, WO 07/039481, WO 2008/138892, WO 2011/080296, WO 2011/080297 or WO 2013/079849.

According to a preferred aspect of the invention, the said esters are prepared from high purity pelargonic acid, preferably greater than 95%, more preferably greater than 98%, and a polyol selected from neopentyl glycol, glycerol or pentaerythritol, through an esterification reaction, which is advantageously performed in the absence of catalyst.

The said esterification is advantageously performed in the presence of a molar excess of pelargonic acid with regard to the moles of polyol, preferably equal to or greater than 30% and less than 70%, working at a temperature of typically between 180 and 240° C., preferably 200-210° C. The water forming during the esterification reaction is advantageously removed from the reaction environment, for example by applying a gradual reduction in pressure; at the end of the reaction the excess acid is removed, preferably by evaporation. The ester so obtained can advantageously undergo purification treatments according to processes known to those skilled in the art, for example using activated carbons and decolouring earths, with a view to eliminating any colour, odour and residual acidity. Examples of decolouring earths which may be used, including in combination with activated carbons, are Grade F-118FF, Grade F76 (marketed by BASF), Minclear N100, Minclear E100 and Pansil 2 (marketed by Tolsa).

In comparison with the esters obtained by ordinary esterification procedures, catalysed by metals, for example tin, the esters obtained by operating in accordance with the procedure described above do not contain metal residues which might have an influence on organoleptic characteristics (e.g. colour, odour) and their stability. They therefore have the particular advantage of a reduced inorganic matter content and require simpler preliminary treatments for use in the cosmetic environment.

By oily component is meant, according to the present application, a lipophilic component which is liquid at ambient temperature (25° C.) and atmospheric pressure, which may be of plant, animal, mineral and/or synthetic origin.

The oily component of the cosmetic compositions according to the invention advantageously comprise the pelargonic acid asters specified above (neopentyl glycol dipelargonate, glycerol tripelargonate, pentaerythritol tetrapelargonate); in addition to these, there may be one or more oils selected from esters, amides, ethers, alcohols and hydrocarbons of natural and/or synthetic origin, silicone oils or their mixtures.

The said oils are typically in liquid form at ambient temperature (25° C.) and atmospheric pressure.

Possible examples of esters of natural origin are triglycerides of saturated or unsaturated fatty acids, such as for example triglycerides of C8 and C10 acids, or their mixtures such as for example those present in vegetable oils. Suitable vegetable oils are for example olive oil, sunflower oil, maize oil, soya oil, castor oil, apricot oil, avocado oil, almond oil, macadamia oil, jojoba oil or karite oil.

Esters of synthetic origin are for example esters of linear and branched carboxylic acids with monoalcohols, such as isononyl isononanoate, isopropyl myristate, 2-ethy hexyl palmitate, isodecyl neopentanoate, isostearyl neopentanoate, 2-octyldodecyl stearate, 2-octyldodecyl erucate or isostearyl isostearate, diisostearyl maleate, C12-15 alkyl benzoate; esters of C7-C10 chain fatty acids with fatty alcohols; hydroxylated esters, such as isostearyl lactate, octyl hydroxystearate, octyldodecyl hydroxystearate; esters of polyols, such as propylene glycol dioctanoate, neopentyl glycol diheptanoate or diethylene glycol diisononanoate and pentaerythrityl tetraisostearate.

One example of an ether is dicaprilyl ether. One example of an amide is dibutyl lauroyl glutamide.

Other examples of oils include fatty alcohols such as octyldodecanol, hexyldodecanol, isostearyl alcohol.

Hydrocarbon oils of natural origin are for example terpene hydrocarbons such as squalene and squalane; hydrocarbon oils of mineral or synthetic origin are for example liquid paraffin and its derivatives such as isoparaffins (e.g. isododecane, isohexadecane, polydecene hydrogenate) and cycloparaffins.

The silicone oils are synthetic compounds based on silicon; they may be volatile or non-volatile, linear or cyclic. Examples of silicone oils are polysiloxanes and their derivatives comprising for example alkyl, alkoxyl or phenyl groups; silicone oils typically used include the polydimethylsiloxanes (Dimethicone), Amodimethicone, Cyclomethicones such as Cyclopentasiloxane and Cyclohexasiloxane, Amino Bispropyl Dimethicone, Aminopropyl Dimethicone, Amodimethicone hydroxystearate, Behenoxy-Dimethicone, C30-45 Alkyl Dimethicone, C24-28 Alkyl Dimethicone, C30-45 Alkyl Methicone, Cetearyl Methicone, Cetyl Dimethicone, Dimethoxysilyl Ethylenediaminopropyl Dimethicone, Hexyl Methicone, Hydroxypropyldimethicone, Stearamidopropyl Dimethicone, Stearoxy Dimethicone, Stearyl Methicone, Stearyl Dimethicone and Vinyl Dimethicone.

Advantageously, the cosmetic compositions according to the invention comprise one or more components deriving from the insaponifiable fraction of vegetable oils (for example carotenoids, xanthophylls, tocopherols, phytosterols, aliphatic and terpene alcohols). Vitamins and active agents of a lipophilic nature may also be present dissolved in the oily component. The cosmetic composition according to the invention may also comprise one or more waxes.

By the term "wax" is meant a lipophilic component which is solid at ambient temperature (25° C.) and atmospheric pressure; the said component imparts rigidity, plasticity and strength to the cosmetic compositions containing it, which are therefore suitable for being prepared in solid form as, for example, sticks.

Waxes suitable for use in the compositions according to this invention are all the waxes typically used in cosmetic compositions. These may be of natural and/or synthetic origin; examples of natural waxes are beeswax or cera alba, carnauba wax, candelilla wax, Japan wax, rice wax, waxes deriving from hydrogenated oils, such as jojoba oil or sunflower or coconut oils, esters of long chain saturated fatty acids with long chain monoalcohols or their glycerides such as cetyl palmitate, cetyl stearate, palmitic and stearic triglycerides.

Examples of mineral or synthetic waxes are lignite wax, microcrystalline wax, paraffin, ozokerite, ceresin, synthetic beeswax, lanolin and their ethers with polypropylene glycols, polyethylene waxes, fatty acid esters having a melting point above 25° C., cetyl esters and polyamides. Silicone waxes such as alkyl or alkoxy-dimethicones or poly(di) methylsiloxanes having a high molecular weight may also be used.

The said waxes are used in quantities which vary depending upon the type of cosmetic product, as known to those skilled in the art, typically between 5% and 35% by weight in the composition. Mixtures of waxes having different melting points are preferably used.

According to a particularly preferred embodiment the lipophilic cosmetic composition according to the invention comprises, with respect to the weight of the cosmetic composition:
  a) from 50 to 99% by weight, preferably from 55 to 95% by weight of an oily component comprising at least one ester selected from neopentyl glycol dipelargonate, glycerol tripelargonate and pentaerythritol tetrapelargonate and their mixtures;
  b) from 1 to 35% by weight, preferably from 5 to 30%, more preferably from 7 to 20%, of one or more waxes;
  c) from 0 to 30% by weight, preferably from 0.1 to 20%, more preferably from 0.1 to 15%, of one or more colouring agents;
  d) from 0 to 3%, preferably from 0.05 to 2% by weight of vitamins and/or antioxidants;
  e) from 0 to 2% by weight, preferably from 0.01 to 1% by weight of one or more preservatives.

The said composition is particularly suitable for the preparation of spreadable lipsticks, butters and lip balms, concealers, foundation creams, cast and stick eye shadows.

The cosmetic composition according to this invention comprising the said oily component characterised in that it comprises at least one ester selected from neopentyl glycol dipelargonate, glycerol tripelargonate, pentaerythritol tetrapelargonate and their mixtures may also comprise one or more of polyolefin, acrylic derivatives, polyamides and/or polyesters oligomers, for example, polybutylene and/or polyisobutylene.

In accordance with this aspect the said oily component preferably comprises between 5 and 65% by weight, more preferably between 10 and 35% by weight, of the cosmetic composition. According to this aspect the said composition may also advantageously comprise suspended powders, colouring agents and antioxidants. Cosmetic compositions of this type are particularly suitable for the preparation of cosmetics such as lip gloss.

By "oligomers" are typically meant oligomers and polymers having a molecular weight below 1000 g/mole that are liquid at ambient temperature (25° C.) and atmospheric pressure, which are responsible for providing brightness and tack to the cosmetic composition. Suitable oligomers are selected from the group comprising polybutenes, polyisobutylenes and hydrogenated polyisobutylenes, polydecenes and hydrogenated polydecenes, polyethylene, polyamides, polyesters. Preferred oligomers are selected from polybutylene, polyisobutylene and/or polyamides.

According to a particularly preferred embodiment the lipophilic cosmetic composition according to the invention comprises, with respect to the weight of the cosmetic composition:
a) from 15 to 85% by weight, preferably from 29 to 80%, of one or more oligomers;
b) from 5 to 65% by weight, preferably from 10 to 35%, of an oily component comprising at least one ester selected from neopentyl glycol dipelargonate, glycerol tripelargonate and pentaerythritol tetrapelargonate and their mixtures;
c) from 0 to 15% by weight, preferably from 2 to 5%, of one or more flow modifiers having suspending power;
d) from 0 to 20% by weight, preferably from 0.1 to 15%, of one or more colouring agents;
e) from 0 to 5% by weight, preferably from 0.1 to 3%, of one or more waxes;
f) from 0 to 3% by weight, preferably from 0.05 to 2%, of vitamins and/or antioxidants;
g) from 0 to 2% by weight, preferably from 0.01 to 1%, of one or more preservatives.

The said composition is particularly suitable for the preparation of lip glosses.

The lipophilic cosmetic composition according to this invention also advantageously comprises one or more sun filters, in quantities of preferably between 0.05% and 35% by weight, preferably between 0.1 and 30%, with respect to the weight of the cosmetic composition. In accordance with this aspect the oily component comprises from 50 to 99% by weight, advantageously from 50 to 90% by weight, of the cosmetic composition.

Sun filters have the function of protecting skin and/or hair from UVA/UVB radiation. These include for example filters or physical screens with reflecting properties such as for example zinc oxide and titanium dioxide, either in the form of nanomaterials or having particles of larger size, silica, kaolin, iron and/or magnesium oxides, and chemical filters, typically organic molecules capable of absorbing and converting the energy of ultraviolet radiation such as cinnamates, benzoimidazoles, benzophenones, benzylidene camphorate, PABA and its derivatives, salicylates, anthranylates, dibenzoyl methanes, octocrylene, triazines such as octyltriazone, bis-ethylhexyloxyphenol methoxyphenyl triazine and diethyl hexyl butamido triazone, natural antioxidants such as vitamin C and vitamin E or synthetic vitamins, such as Tinogard TT, or their combinations.

Physical and chemical filters may be of natural origin (such as for example gamma orizanol) or synthetic, and be used alone or more advantageously in combination.

Specific examples of sun filters suitable for use in the compositions according to the invention are octyl-methoxycinnamate, 2-ethyl-hexyl-4-dimethylaminobenzoate, butylmethoxy-dibenzoylmethane, octyl triazone, diethyl hexylbutamido triazone, ethyl hexyl salicylate, zinc oxide, titanium dioxide, or their combinations.

In accordance with a particularly preferred embodiment the lipophilic cosmetic composition according to the invention comprises, with respect to the weight of the cosmetic composition:
a) from 50 to 99% by weight, preferably from 50 to 90%, of an oily component comprising at least one ester selected from neopentyl glycol dipelargonate, glycerol tripelargonate and pentaerythritol tetrapelargonate and their mixtures;
b) from 0.05 to 35% by weight, preferably from 0.1 to 30%, of one or more sun filters;
c) from 0 to 30% by weight, preferably from 5 to 25%, more preferably from 7 to 20%, of one or more waxes;
d) from 0 to 30% by weight, preferably from 0.1 to 3% of one or more colouring agents;
e) from 0 to 2% by weight, preferably from 0.01 to 1%, of one or more preservatives.

The said composition is particularly suitable for the preparation of sun protection products, for example sun protection sticks, oils and butters.

Thanks to the properties of the pelargonic acid esters present in the oily component the cosmetic compositions according to this aspect of the invention have the particular advantage that they ensure optimum dispersion for the sun filters, whose protection factor they can help to increase. Additionally, they have shown higher solubilisation and dispersion rates when compared to some of the commonly used oily solvents/dispersants. They are therefore suitable for the preparation of water-free sun products, cosmetics for the care of the body and hair, and make-up products having an anti-aging protective action.

Particularly suitable for this purpose are compositions comprising pentaerythritol tetrapelargonate and glycerol tripelargonate or their mixtures, which have particularly marked flow and viscosity properties and which are particularly soft. More preferred are compositions comprising glycerol tripelargonate.

The cosmetic compositions according to this invention may contain water in a quantity not exceeding 20%; preferably the water content is less than 5% by weight.

According to a preferred aspect the cosmetic composition according to the invention advantageously comprises one or more colouring agents or dyes, in a quantity of preferably between 0.1% and 35% by weight, more preferably of between 0.1 and 30% by weight, even more preferably between 0.1 and 20% by weight. The said colouring agents may be soluble or insoluble in water, soluble or insoluble in fats, mineral or organic, natural or synthetic, and have the function of colouring or opacifying the cosmetic composition. Examples of suitable colouring agents are pigments, lacquers or pearls, which may be used as such or after surface treatments intended for example to modify water-repellence or hydrophilic properties. The pigments include derivatives of metals of an inorganic nature, for example oxides of iron, cerium, chromium, titanium, zinc or zirconium, silicates (e.g. micas), sulfosilicates (e.g. ultramarine) and their combinations, and molecules of an organic nature, such as for example plant extracts. By the term "pearls" are meant special pigments capable of developing reflection and refraction phenomena with light, which may be iridescent or non-iridescent, either organic (such as guanine, CI 75170) or inorganic (such as bismuth oxychloride, CI 77163, or sericite, CI 77019).

Thanks to the properties of the pelargonic acid esters present in the lipophilic component the cosmetic compositions according to the invention have the particular advantage that they ensure optimum dispersion of the lipophilic pigments and coated pigments, whose colour they can help to intensify.

The cosmetic compositions according to this invention may also contain other additives typically used in the field of cosmetics, such as antioxidants and/or vitamins, sun filters for product protection, preservatives, pH modifiers, humectants (e.g. glycerine, sorbitol, glycols, polyethylene glycols), conditioners, chelating agents, flow modifiers, texturising agents, film-forming agents, silicones, perfumes, essential oils, and active ingredients, in particular cosmetically and/or dermatologically active ingredients.

Each additive may be present in a quantity from 0 to 35%, preferably up to 20% by weight, more preferably up to 10% with respect to the total weight of the cosmetic composition.

By the term "preservatives" according to the invention are meant natural or synthetic substances having the primary function of inhibiting the growth of microorganisms in the cosmetic composition. The list of permitted preservatives makes reference to Appendix V to EC Regulation 1223/2009. The maximum permitted percentages used, any limitations and methods of use may be found within the document. The most widely used preservatives include for example: benzoic acid, propionic acid, salicylic acid, sorbic acid and their salts, p-hydroxybenzoic acid, its salts and esters, dehydroacetic acid, potassium sorbate, phenoxyethanol, imidazolidinyl urea. In combination or as an alternative to the said preservatives the cosmetic compositions according to the invention may also contain other substances capable of contributing to inhibition of the growth of microorganisms such as for example honey, essential oils such as extracts of rosemary, *Melaleuca alternifolia* and thyme, and complexing agents such as EDTA.

The cosmetic composition according to some aspects of the invention advantageously comprises one or more flow modifiers. By "flow modifiers" are meant gelling agents, thickeners, dispersants, suspended powders and other substances which influence rheological behaviour and, as a consequence, the stability and application of the cosmetic composition.

They may be of natural or synthetic, mineral or organic nature. Among the organic flow modifiers, natural polymers such as alginates, carrageenans, agar agar, pectins, starches, cellulose and their chemically modified derivatives, synthetic polymers such as acrylic polymers, which may or may not be hydrophobically modified, hydrophobically modified urethanes, alkene/styrene copolymers, polyethylene, polyamides, polyesters, polyethylene glycol derivatives, and fatty acids and their salts are preferred. Examples of inorganic flow modifiers are clays, silicas and their modified derivatives, magnesium and/or aluminium silicate.

A class of flow modifiers which is particularly suitable for use in the compositions according to this invention comprises suspended powders.

The cosmetic compositions according to this invention may be in solid, paste or liquid form.

The cosmetic compositions according to the invention may be prepared according to processes known to those skilled in the art in the cosmetics sector.

In accordance with a preferred method of preparation the ingredients of the cosmetic composition are mixed, advantageously after any solid components have been brought to their melting points, using specific equipment, such as for example three-cylinder refiners, which make it possible for any additives to be finely dispersed.

The cosmetic compositions according to the invention find application in coloured or colourless cosmetic products for the skin and skin annexes and in particular for the care, make-up, cleansing and sun protection. Preferred applications are lipsticks, foundation creams, concealers, butters and balms for the lips and/or body, lip gloss, stick sun protection products, sun protection oils, cleaning oils, baby oils and oils for special treatments.

One aspect of this invention relates to lipophilic cosmetic compositions containing neopentyl glycol dipelargonate. The said cosmetic compositions have a light, soft and silky touch, and provide an opaque finish and a thin film, being therefore particularly suitable, for example, for the application of opaque lipsticks.

Another aspect of this invention relates to lipophilic cosmetic compositions containing glycerol tripelargonate. The said cosmetic compositions have good flow and a light dry, non-unctuous touch, providing a slightly brilliant finish. They are therefore suitable, for example, for make-up products, in particular opaque ones.

Another aspect of this invention relates to lipophilic cosmetic compositions containing pentaerythritol tetrapelargonate. The said ester is characterised by appreciable emollient properties and imparts a rich but non-unctuous touch, flow properties and homogeneity, excellent dispersion of UVA/UVB sun filters upon the cosmetic compositions, being particularly suitable for application in sun products.

Another aspect of this invention relates to lipophilic cosmetic compositions containing at least two esters selected from neopentyl glycol dipelargonate, glycerol tripelargonate and pentaerythritol tetrapelargonate. Lipophilic cosmetic compositions comprising binary or ternary mixtures of the abovementioned esters, such as for example mixtures of neopentyl glycol dipelargonate and glycerol tripelargonate or mixtures of neopentyl glycol dipelargonate and pentaerythritol tetrapelargonate, or mixtures of glycerol tripelargonate and pentaerythritol tetrapelargonate, or again mixtures of neopentyl glycol dipelargonate, glycerol tripelargonate and pentaerythritol tetrapelargonate are therefore an object of the invention.

This invention will now be illustrated in detail by the following non-limiting examples.

EXAMPLES

The esters used in the following examples have been prepared using pelargonic acid originating from the oxidative cleavage of sunflower oil having a high oleic acid content. In particular pelargonic acid obtained according to the process described in patent application WO 2011080296 has been used at the end of stage c) of separation of the monocarboxylic acids from the triglycerides containing more than one acid function and subsequent rectification to remove the fraction comprising light monocarboxylic acids, such as described in Example 1. The pelargonic acid used has a purity of 99%.

Preparation of Neopentyl Glycol Dipelargonate, Glycerol Tripelargonate and Pentaerythritol Tetrapelargonate Esters The esterification reactions for synthesis of the three esters were carried out in the absence of catalyst and with a molar excess of pelargonic acid of 30% molar with respect to the polyol used (neopentyl glycol, glycerine or pentaerythritol). In order to favour the removal of esterification water the temperature of the acid/polyol mixtures was increased to 200-210° C. in the course of the reactions; once this temperature had been reached gradual vacuum was applied up to 100 mbar in order to favour conversion of the reagents. Once the reactions were complete, after a quantity of reaction water corresponding to the theoretical quantity had been obtained, the excess acid was recovered by evaporation, keeping the temperature around 180-200° C. with a vacuum of 5 to 10 mbar.

The products then underwent decolouring treatment with activated carbon and decolouring earth and neutralisation through the addition of a quantity of calcium hydroxide and water (in a 1:1 ratio by weight) of between 1 and 2% by weight with regard to each ester, heating to 60° C. with stirring for 30 minutes. After water had been completely removed by heating to 80-100° C. in a vacuum, a filtering earth (Celite 512; 1% by weight with respect to the ester) was added with stirring, and the liquid was filtered under vacuum on a bed of the same earth, obtaining a clear product.

Measurements of acidity made in accordance with standard ASTM D664 showed a residual acidity of less than 0.1 mg KOH/g for each of the three esters.

The following tables show examples of cosmetic compositions according to the invention. A list of ingredients (in accordance with the INCI nomenclature) and the percentage composition by weight of each ingredient in relation to the total weight of the composition are shown for each composition.

Stability measurements were performed in accordance with the guidelines provided in UNIPRO Bulletin No. 32 on the basis of the sensory evaluation of the organoleptic characteristics of the composition (odour, colour, appearance) after 3 months on samples held at 4° C., 40° C. and ambient temperature/light (25° C.).

Examples 1 (Comparison)-2 (Body and Hair Oil)

Ingredients:

|   | INCI | Example 1 (comparison) | Example 2 |
|---|---|---|---|
| A | Isononyl Isononanoate | 45.9 | 45.9 |
|   | Ethylhexyl Palmitate | 20.0 | 20.0 |
|   | Olive Glyceride | 8.0 | — |
|   | Glycerol tripelargonate | — | 8.0 |
|   | Prunus Armeniaca Kernel Oil | 7.0 | 7.0 |
|   | O-Cymen-5-Ol | 0.1 | 0.1 |
|   | Propanediol Dicaprylate | 15.0 | 15.0 |
| B | Tocopherol | 1.0 | 1.0 |
|   | Linseed Acid | 1.0 | 1.0 |
|   | Tocopheryl Acetate | 1.0 | 1.0 |
|   | Parfum | 1.0 | 1.0 |

Preparation:

The ingredients in group A were weighed and placed together in a mixer with stirring, heating to a temperature of 45+/−2° C. The ingredients in group B were weighed and added to mixture A one at a time, mixing for 10 minutes after each addition. Continuing with constant stirring, the A+B mixture so obtained was cooled to ambient temperature and transferred to suitably provided containers.

Both the compositions obtained took the form of yellow oil and showed the same performance. Their organoleptic properties also remained unchanged following the 3 months' stability tests at 4° C., 40° C. and 25° C.

Examples 3 (Comparison)-4 (SPF50+ Sun Stick)

Ingredients:

|   | INCI | Example 3 (comparison) | Example 4 |
|---|---|---|---|
| A | Paraffinum Liquidum | 29.21 | 29.21 |
|   | Octyldodecanol | 3.50 | — |
|   | Pentaerythritol tetrapelargonate | — | 3.50 |
|   | Cera Microcristallina | 2.80 | 2.80 |
|   | Copernicia Cerifera (Carnauba) Wax | 3.50 | 3.50 |

-continued

|   | INCI | Example 3 (comparison) | Example 4 |
|---|---|---|---|
|   | Ozokerite | 6.84 | 6.84 |
|   | Synthetic Beeswax | 4.10 | 4.10 |
|   | Paraffin | 5.35 | 5.35 |
|   | Petrolatum | 6.00 | 6.00 |
|   | Candelilla cera | 5.50 | 5.50 |
|   | Olive Glycerides, Ceramide NP | 1.00 | 1.00 |
|   | Olive Glycerides | 1.00 | 1.00 |
|   | O-Cymen-5-Ol | 0.10 | 0.10 |
| B | Octocrylene | 10.00 | 10.00 |
|   | Ethylhexyl salicylate | 4.70 | 4.70 |
|   | Butyl Methoxydibenzoylmethane | 5.00 | 5.00 |
|   | Titanium Dioxide (CI77891), Silica | 11.00 | 11.00 |
| C | Tocopheryl Acetate | 0.20 | 0.20 |
| D | Parfum | 0.20 | 0.20 |

Preparation:

The ingredients in group A were weighed and placed in the fat melter one at a time, heating them to a temperature of 95+/−2° C., with gentle stirring until the waxes were completely melted. The system was then cooled for 80+/−2° C. with constant gentle stirring, and the components in group B were then added one at a time, mixing after each addition. The system was then cooled to 75+/−2° C. and ingredient C, and then ingredient D were added, continuing stirring until dispersion was homogeneous.

The mixture so obtained was then cooled to ambient temperature and transferred to suitably provided containers.

The two compositions were prepared in stick form. Both were of an ivory colour and had the same performance. They also passed the 3 months' stability tests at 4° C., 40° C. and 25° C.

Examples 5 (Comparison)-6 (Lipstick)

Ingredients:

| INCI | Example 5 (comparison) | Example 6 |
|---|---|---|
| Pentaerythrityl Tetraisostearate | 35.18 | 35.18 |
| Octyldodecanol | 12.19 | 12.19 |
| Isostearyl Isostearate | 10.5 | 10.5 |
| Candelilla Cera | 10 | 10 |
| Cera Alba | 9 | 9 |
| Polyglyceryl-2 Isostearate/Dimer Dilinoleate Copolymer | 6 | 6 |
| Titanium Dioxide (CI77891) | 5.6 | 5.6 |
| Caprylic/Capric Triglycerides | 5 | — |
| Glycerol tripelargonate | — | 5 |
| Diisostearyl Malate | 4 | 4 |
| Copernicia Cerifera (Carnauba) Wax | 1.76 | 1.76 |
| CI 75470 (Carmine) | 0.4 | 0.4 |
| Tocopheryl Acetate | 0.2 | 0.2 |
| O-Cymen-5-Ol | 0.12 | 0.12 |
| Aroma | 0.05 | 0.05 |

The cosmetic composition according to the invention containing glycerol tripelargonate (Example 6) prepared in the form of lipstick showed the same performance as the comparison composition of Example 5, which contained triglycerides of capric and caprylic acids.

Example 7 (Massaging Oil with Glycerol Tripelargonate)

A massaging oil was prepared by mixing glycerol tripelargonate (80% by weight) with almond oil (Apricot Kernel Oil, 20% by weight) until a homogeneous mixture was obtained.

Examples 8 (Comparison)-11 (Stick Concealer)

Ingredients:

| | INCI | Example 8 (comparison) | Example 9 | Example 10 | Example 11 |
|---|---|---|---|---|---|
| A | C12-15 alkyl benzoate | 25.54 | — | — | — |
| | Glycerol tripelargonate | — | 44.52 | — | 8 |
| | Pentaerythritol tetrapelargonate | — | — | — | 4 |
| | Neopentyl glycole dipelargonate | — | — | 44.52 | 32.52 |
| | Ethylhexyl Palmitate | 10.98 | — | — | — |
| | Isononyl Isononanoate | 8.00 | — | — | — |
| | Dimethicone | 4.00 | 4 | 4 | 4 |
| | Candelilla Cera | 2.99 | 2.99 | 2.99 | 2.99 |
| | Copernicia Cerifera (Carnauba) Wax | 2.00 | 2 | 2 | 2 |
| B | Aluminum Starch Octenylsuccinate | 4.00 | 4 | 4 | 4 |
| | Polyethylene | 6.00 | 6 | 6 | 6 |
| | Talc | 6.00 | 6 | 6 | 6 |
| | Stearic Acid | 2.00 | 2 | 2 | 2 |
| | Microcrystalline Wax | 1.75 | 1.75 | 1.75 | 1.75 |
| | Silica | 0.94 | 0.94 | 0.94 | 0.94 |
| | Synthetic Wax | 0.15 | 0.15 | 0.15 | 0.15 |
| | Kaolin | 2.00 | 2 | 2 | 2 |
| | Polyglyceryl-3 Diisostearate | 2.00 | 2 | 2 | 2 |
| | Trimethylsiloxyphenyl Dimethicone | 1.95 | 1.95 | 1.95 | 1.95 |
| | Sorbitan Sesquiisostearate | 1.95 | 1.95 | 1.95 | 1.95 |
| | CI 77891 (Titanium Dioxide) | 1.98 | 1.98 | 1.98 | 1.98 |
| | CI 77491 (Iron Oxides) | 2.59 | 2.59 | 2.59 | 2.59 |
| | CI 77492 (Iron Oxides) | 4.47 | 4.47 | 4.47 | 4.47 |
| | CI 77499 (Iron Oxides) | 0.24 | 0.24 | 0.24 | 0.24 |
| | CI 77007 (Ultramarines) | 3.77 | 3.77 | 3.77 | 3.77 |
| C | Isododecane | 2.50 | 2.5 | 2.5 | 2.5 |
| | Polymethyl Methacrylate | 2.00 | 2 | 2 | 2 |
| | Tocopheryl Acetate | 0.20 | 0.2 | 0.2 | 0.2 |

Preparation:

The ingredients in group A were placed in a mixer and heated to a temperature of 90° C. On reaching this temperature the ingredients in phase B were added with stirring, mixing until the mixture was completely homogenised. Continuing to heat in order to hold the temperature at around 80° C., all the ingredients in group C were added in the order in which they are shown in the table, continuing to stir until a homogeneous mixture was obtained. The mixture so obtained was then poured into moulds and allowed to cool.

Examples 12 (Comparison)-15 (Lip Gloss)

Ingredients:

| | INCI | Example 12 (comparison) | Example 13 | Example 14 | Example 15 |
|---|---|---|---|---|---|
| A | Paraffinum Liquidum | 40.22 | 40.22 | 40.22 | 40.22 |
| | Diethylhexyl Sebacate | 20 | — | — | — |
| | Neopentyl glycol dipelargonate | — | 20 | — | — |
| | Pentaerythritol tetrapelargonate | — | — | 20 | — |
| | Glycerol tripelargonate | — | — | — | 20 |
| B | Hydrogenated Styrene/Isoprene Copolymer | 3.9 | 3.9 | 3.9 | 3.9 |
| | Silica Dimethyl Sililate | 1 | 1 | 1 | 1 |
| | Polybutene | 33.5 | 33.5 | 33.5 | 33.5 |
| | Mica | 0.55 | 0.55 | 0.55 | 0.55 |
| | CI 77491 (Iron Oxides) | 0.02 | 0.02 | 0.02 | 0.02 |
| | CI 15850 (Red 6) | 0.01 | 0.01 | 0.01 | 0.01 |
| | CI 77891 (Titanium Dioxide) | 0.2 | 0.2 | 0.2 | 0.2 |
| C | Pentaerythrityl Tetra-Di- t-Butyl Hydroxycinnamate | 0.1 | 0.1 | 0.1 | 0.1 |
| | Tocopheryl Acetate | 0.1 | 0.1 | 0.1 | 0.1 |
| | Aroma | 0.4 | 0.4 | 0.4 | 0.4 |

Preparation:

The ingredients in group A were placed in a mixer and heated to a temperature of 85° C. On reaching the temperature the ingredients in group B were added with stirring, mixing until the mixture was completely homogenised. Heating was stopped, while continuing to stir, and when the temperature of the mixture fell below 50° C. the ingredients in group C were added. Stirring was continued until the product was completely homogenised.

Examples 16-19 (Lipstick Evaluation)

Four lipophilic cosmetic compositions were prepared in the form of lipsticks according to the following ingredients list:

| | INCI | Example 16 | Example 17 (comparison) | Example 18 | Example 19 (comparison) |
|---|---|---|---|---|---|
| A | Candelilla cera | 10.00 | 10.00 | 10.00 | 10.00 |
| | Copernicia Cerifera Cera | 1.76 | 1.76 | 1.76 | 1.76 |
| | Cera alba | 8.82 | 8.82 | 8.82 | 8.82 |
| | Octyldodecanol | 12.19 | 12.19 | — | 12.19 |
| | Ethylhexyl Stearate | 6.12 | 6.12 | 6.12 | 6.12 |
| | Diisostearyl malate | — | 15.60 | — | 15.60 |
| | Glycerol tripelargonate | — | — | 10.50 | — |
| | Pentaerythritol tetrapelargonate | 15.60 | — | 52.30 | — |
| | Polyglyceryl-2 Isostearate/Dimer Dilinoleate Copolymer | 4.71 | 4.71 | — | 4.71 |
| | Pentaerythrityl Tetraisostearate | 30.30 | 30.30 | — | 20.30 |
| | Phenyl Dimethicone | — | — | — | 10.00 |
| | Tocopheryl acetate | 0.50 | 0.50 | 0.50 | 0.50 |
| B | Synthetic wax, Red 7 Lake, Isopropyl Titanium triisostearate | 5.80 | 5.80 | 5.80 | 5.80 |

-continued

| INCI | Example 16 | Example 17 (comparison) | Example 18 | Example 19 (comparison) |
|---|---|---|---|---|
| Synthetic wax, Titanium Dioxide, Isopropyl Titanium triisostearate | 4.20 | 4.20 | 4.20 | 4.20 |

The four resulting compositions were subjected to a sensory evaluation. A panel of 20 individuals (women) was required to test the lipsticks and provide a rating from 1 to 5 on the properties listed in the table below.
Evaluation Scale:
  5: Excellent
  4: Very good
  3: Good
  2: Fair
  1: Poor

| Sensory evaluation | Example 16 | Example 17 (comparison) | Example 18 | Example 19 (comparison) |
|---|---|---|---|---|
| Flowability | 4 | 3 | 5 | 3 |
| Fullness | 5 | 4 | 5 | 4 |
| Softness | 4 | 3 | 5 | 3 |
| Adherence | 4 | 3 | 4 | 3 |
| Uniformity of the film | 5 | 3 | 5 | 4 |
| Gloss effect | 4 | 4 | 5 | 5 |

The composition of Example 16 comprising pentaerythritol tripelargonate showed a better spreadability and a more intense and homogeneous color due to a better pigment dispersion, good adherence on lips and a comparable gloss effect when compared to the composition of Example 17.

The composition of Example 18, comprising a mixture of glycerol tripelargonate and pentaerythritol tripelargonate showed even higher softness and flowability and a gloss effect comparable to that achieved by the composition of Example 19, which comprises phenyl dimethicone.

Example 20—Pigments Dispersion

Black Iron Oxide particles (CI77499, commercially available as YPC335200 from Yipin) were dispersed in each of the ester oils of the present invention and in ester oil commonly used as cosmetic ingredients. Each sample of powder particles was wetted by the dropwise addition of one ester oil and then vigorously blended using a spatula until the wet point and the flow point were reached.

The wet point is defined as the minimum volume of dispersant solution to produce a soft coherent mass; the further minimum addition of dispersant solution to produce flow or falling off of the homogeneous mass from the vertical blade of a horizontally held spatula determines the flow point.

The amounts of dispersant solution (i.e. ester oil) needed to reach the wet point (Wp) and the flow point (Fp) were recorded and reported in the table below, expressed in grams per 100 g of pigment.

| Pigment dispersion | Wp (g) | Fp (g) |
|---|---|---|
| Isononyl Isononanoate | 50.00 | 145.00 |
| Caprylic/Capric Triglyceride | 60.00 | 130.00 |
| C12-15 Alkyl Benzoate | 60.00 | 143.00 |
| Neopentyl glycol dipelargonate | 61.00 | 166.00 |
| Glycerol tripelargonate | 60.00 | 100.00 |
| Pentaerythritol tetrapelargonate | 62.00 | 132.00 |

The ester oils of the invention showed dispersion properties comparable to those of commonly used cosmetic ingredients. Surprisingly, glycerol tripelargonate has revealed a Fp significantly close to the Wp, demonstrating dispersion properties even better than those of Caprylic/Capric Triglyceride. This minimum difference results in a considerable advantage as it enables significant cost savings on the final composition (wherein about 30% less solvent is required). The dispersions thus prepared were tested on the forearm to assess the differences in terms of smoothness, writing capabilities, color consistency, gloss effect. A scale from 1 (low) to 5 (high) was used. The sensory evaluation test results are reported in the table below.

| Sensory evaluation | Isononyl Isononanoate | Caprylic/Capric Triglyceride | C12-15 Alkyl Benzoate | Neopentyl glycol dipelargonate | Glycerol tripelargonate | Pentaerythritol tetrapelargonate |
|---|---|---|---|---|---|---|
| Flowability | 4 | 4 | 2 | 2 | 5 | 4 |
| Writing capability/color intensity | 2 | 4 | 4 | 3 | 4 | 4 |
| Film evenness | 2 | 3 | 4 | 4 | 4 | 4 |
| Gloss effect | 2 | 3 | 4 | 2 | 5 | 5 |

Glycerol tripelargonate and pentaerythritol tetrapelargonate showed flowability, film evenness and gloss effect higher than those of commonly used ester oils.

Example 21—UV Filters Dispersion

The dispersibility of a solid UV filter in different ester oils was tested using Titania (TiO$_2$, commercially available as Titanio Biossido Anatasio from A.C.E.F.). Various ratios of filter/ester (1% and 10% TiO$_2$) were prepared under stirring at 70° C. for 30 minutes. The dispersions were then observed after a storage period of 0 hours ($t_0$) and 24 hours ($t_{24}$) at ambient temperature (25° C.) to check for the formation of any sediment deposit. Results for each ester are shown in the table below (D=homogeneous dispersion; S=sediment deposit).

| Filters dispersion | $t_0$ | | $t_{24}$ | |
|---|---|---|---|---|
| | 1% | 10% | 1% | 10% |
| Isononyl Isononanoate | D | D | S | S |
| Caprylic/Capric Triglyceride | D | D | S | S |
| C12-15 Alkyl Benzoate | D | D | S | S |
| Neopentyl glycol dipelargonate | D | D | S/D | S/D |
| Glycerol tripelargonate | D | D | D | S/D |
| Pentaerythritol tetrapelargonate | D | D | D | D |

The dispersant capability of the pelargonic acid esters of the invention was equivalent to that of commonly used esters such as Isononyl Isononanoate, Caprylic/Capric Triglyceride and C12-15 Alkyl Benzoate.

Glycerol tripelargonate and pentaerythritol tetrapelargonate showed an even better dispersion of Titania compared with reference solvents.

Example 22—UV Filters Solubility

The solubility of the chemical UV filter Butyl methoxydibenzoylmethane (CAS No. 70356-09-1, commercially available as PARSOL® 1789 from DSM) in different ester oils was tested. Various ratios of solute/solvent (5%, 10%, 20% and 30% by weight; total amount filter+solvent: 10 g) were prepared in glass bottles in a water bath at 60° C. The solutions were then observed after a storage period of 2 hours at 20° C. to check for the formation of any sediment deposit. Once identified the solubility range, which ranged between 10-20% for each filter/solvent couple, the maximum concentration of soluble filter in each ester was determined by making repeated additions of lower amounts of the filter to the solutions at 10%, until the formation of precipitate was observed. Each addition was carried out at a temperature of 60° C. and followed by cooling. The solutions were allowed to stand at the constant temperature of 20° C. for two hours before checking for precipitation (by visual determination).

Results for each ester are shown in the table below:

| Filters solubility | % w/w, 20° C. |
|---|---|
| Caprylic/Capric Triglyceride | 14 |
| C12-15 Alkyl Benzoate | 14 |
| Neopentyl glycol dipelargonate | 18 |
| Glycerol tripelargonate | 18 |
| Pentaerythritol tetrapelargonate | 18 |

The solubility values of Butyl methoxydibenzoylmethane in the three pelargonic acid esters at 20° C. was equivalent and considerably higher than that in commonly used esters such as Caprylic/Capric Triglyceride and C12-15 Alkyl Benzoate.

Example 23—UV Filters Solubility

The solubility of the chemical UV filter Benzophenone-3 (CAS No. 131-57-7, commercially available as UVASORB® MET from 3V Sigma) in pentaerythritol tetrapelargonate and in a ternary mixture of neopentyl glycol dipelargonate, glycerol tripelargonate and pentaerythritol tetrapelargonate (in a weight ratio of 1:1:1) was determined at 20° C. as described in Example 22.

The solubility value of Benzophenone-3 in pentaerythritol tetrapelargonate was of 14% w/w at 20° C., while the corresponding solubility value of the same filter in the ternary mixture was of 19% w/w. The mixture of pelargonic acid esters according to the invention therefore revealed a surprisingly high ability to solubilize UV filters when compared to the one of the individual ester.

The invention claimed is:

1. A cosmetic lipophilic composition comprising less than 20% by weight of an aqueous component and 50 to 99% by weight of an oily component wherein the said oily component comprises glycerol tripelargonate, the cosmetic composition further comprising between 0.1% and 35% by weight of one or more colouring agents or dyes with respect to the weight of the cosmetic composition or between 0.1% and 35% by weight with respect to the weight of the cosmetic composition of one or more sun filters, or a combination thereof.

2. The cosmetic composition according to claim 1 wherein the said oily component further comprises oils selected from the group consisting of esters, ethers, alcohols and hydrocarbons of natural origin, hydrocarbons of synthetic origin, silicone oils, and mixtures thereof.

3. The composition according to claim 1 further comprising at least a wax.

4. The composition according to claim 1 further comprising one or more additives selected from the group consisting of antioxidants, vitamins, sun filters for the product protection, preservatives, pH modifiers, humectants, conditioners, chelating agents, flow modifiers, texturizers, film-forming agents, silicones, perfumes, essential oils, cosmetic and/or dermatological active ingredients and mixtures thereof.

5. The cosmetic composition according to claim 1 further comprising one or more oligomers.

6. A method for the care, the make-up, or for the cleansing of skin or skin appendages which comprises applying to the skin or skin appendages a cosmetic composition according to claim 1.

7. A method for the preparation of a composition selected from the group consisting of lipsticks, butters, balms for the lips, balms for the body, lip glosses, foundations, concealers, sun sticks, sun oils, cleaning oils, baby oils, and oils for special treatments, which comprises mixing together the following: less than 20% by weight of an aqueous component and 50 to 99% by weight of an oily component, between 0.1% and 35% of one or more colouring agents or dyes, one or more sun filters or a combination thereof, wherein the oily component comprises glycerol tripelargonate.

8. A method for the protection from the sun which comprises applying to skin or skin appendages the cosmetic composition according to claim 1.

9. The cosmetic composition according to claim 1, which comprises 55 to 95% by weight of the oily component.

10. The cosmetic composition according to claim 1, which comprises 50 to 90% by weight of the oily component.

* * * * *